United States Patent [19]

Stricker et al.

[11] Patent Number: 4,459,279

[45] Date of Patent: Jul. 10, 1984

[54] RETARD FORM OF PHARMACEUTICALS WITH INSOLUBLE POROUS DIFFUSION COATINGS

[75] Inventors: Herbert Stricker, Ingelheim; Bernhard Freund, Gau-Algesheim; Heribert Harwalik, Ingelheim; Karl L. Rominger, Ingelheim; Siegfried Darda, Ingelheim; Volkmar Häselbarth, Ingelheim; Dietrich Arndts; Wolf D. Bechtel, both of Appenheim; Gerhard Bozler, Biberach; Rolf Brickl, Biberach; Peter Gruber, Biberach, all of Fed. Rep. of Germany

[73] Assignee: Boehringer Ingelheim GmbH, Ingelheim am Rhein, Fed. Rep. of Germany

[21] Appl. No.: 409,131

[22] Filed: Aug. 18, 1982

Related U.S. Application Data

[60] Division of Ser. No. 273,643, Jun. 15, 1981, Pat. No. 4,361,546, which is a continuation of Ser. No. 194,852, Oct. 7, 1980, abandoned, which is a continuation of Ser. No. 57,499, Jul. 13, 1979, abandoned.

[30] Foreign Application Priority Data

| Jul. 15, 1978 | [DE] | Fed. Rep. of Germany | 2831164 |
| Aug. 19, 1978 | [DE] | Fed. Rep. of Germany | 2836355 |
| Aug. 19, 1978 | [DE] | Fed. Rep. of Germany | 2836356 |
| Aug. 19, 1978 | [DE] | Fed. Rep. of Germany | 2836357 |
| Aug. 19, 1978 | [DE] | Fed. Rep. of Germany | 2836358 |
| Aug. 19, 1978 | [DE] | Fed. Rep. of Germany | 2836387 |
| Aug. 19, 1978 | [DE] | Fed. Rep. of Germany | 2836388 |
| Aug. 19, 1978 | [DE] | Fed. Rep. of Germany | 2836419 |
| Aug. 19, 1978 | [DE] | Fed. Rep. of Germany | 2836477 |
| Feb. 14, 1979 | [DE] | Fed. Rep. of Germany | 2905602 |

[51] Int. Cl.$^3$ .............................................. A61K 27/12
[52] U.S. Cl. ......................................... 424/19; 424/21; 424/22; 424/32; 424/33
[58] Field of Search ................................. 424/19–22, 424/32–33, 35, 37

[56] References Cited

U.S. PATENT DOCUMENTS

| 2,853,420 | 9/1958 | Lowey | 424/19 |
| 2,928,770 | 3/1960 | Bardani | 424/19 |
| 2,971,889 | 2/1961 | Swintosky | 424/31 |
| 3,247,066 | 4/1966 | Milosovich | 424/19 |
| 3,344,029 | 9/1967 | Berger | 424/19 |
| 3,371,015 | 2/1968 | Sjogren et al. | 424/35 |
| 3,538,214 | 11/1970 | Polli et al. | 424/19 |
| 3,835,221 | 9/1974 | Fulberth et al. | 424/20 |
| 3,917,813 | 11/1975 | Pedersen | 424/20 |
| 4,083,949 | 4/1978 | Benedickt | 424/19 |
| 4,361,546 | 11/1982 | Stricker et al. | 424/19 |

OTHER PUBLICATIONS

Spitael, Pharm. Ind. 39(5): 502–505 (1977) "Factors Affecting the Dissolution Rate of Enteric Coatings".

*Primary Examiner*—Shep K. Rose
*Attorney, Agent, or Firm*—Hammond & Littell, Weissenberger & Dippert

[57] ABSTRACT

A pharmaceutical dosage unit retard form having a constant, pH-independent release rate of active ingredient, consisting of a core comprising an active ingredient, and a semi-permeable diffusion coating over the core, where the coating consists of a water-insoluble film-former, a water-soluble polymer and eventually an acid-insoluble polymer incorporated therein.

6 Claims, No Drawings

RETARD FORM OF PHARMACEUTICALS WITH INSOLUBLE POROUS DIFFUSION COATINGS

This application is a divisional of U.S. patent application Ser. No. 273,643, filed June 15, 1981 now U.S. Pat. No. 4,361,546, which in turn is a continuation of U.S. patent application Ser. No. 194,852, filed Oct. 7, 1980 now abandoned, which in turn is a continuation of U.S. patent application Ser. No. 057,499, filed July 13, 1979 now abandoned.

This invention relates to a pharmaceutical retard form of constant, pH-independent release rate with a semipermeable diffusion-coating which has been produced under standard conditions, as well as to a core covered therewith, where an acid medium opitionally prevails.

Retardation of the release rate of pharmaceuticals has been described in numerous publications; a survey of the most important principles applied therewith is given, for example, in German Pat. No. 1,467,781.

The ideal oral depot form must act like a permanent intravenous infusion, that is, it must maintain (after a quick increase in the beginning) a blood level as constant as possible for the desired duration of activity of the medicament.

In practice, various factors make it difficult to approach this ideal, factors acting upon a preparation to be taken orally during the passage through the gastro-intestinal tract (differing from intravenous administration). Here are to be mentioned, for example, the pH-gradient, the motility, the enzyme content as well as the electrolyte and water content of the gastro-intestinal tract.

In order to obtain a constant release of the active substance [reaction of zero order, see Soliva and Speiser, Pharmaceutica Acta Helvetiae 41, 176–191 (1966)] there is applied more and more the principle of covering cores containing active substances with semi-permeable diffusion coatings. However, in this manner a release of active substance free from exterior influences, especially from the pH-value in the range of the gastrointestinal tract, cannot be obtained. Solubility of substances with $pk_a$-values, which are in the pH-range of the stomach (1–3) or the intestines (5–8) varies often in this range. This acts upon the speed of diffusion of active substance through the barrier of the casing.

It has been tried to solve this problem by developing for each active substance a casing adjusted individually for it. However, this is connected with considerable work and costs.

There has already been proposed to obtain a pH-independent constant release rate without adapting the coat individually by means of bringing an active component into a mixture with buffer salts in form of smaller particles, which are covered with materials that are film-forming, allow for the diffusion of gastric and intestinal fluids, but do not dissolve these fluids (see German Offenlegungsschrift No. 2,414,868).

However, corresponding trials have shown that in this way only in the beginning of release a compensation of pH-dependence can be reached for a limited period of time; afterwards, the original pH-dependence occurs relatively quickly again.

We have discovered that for depot forms with semi-permeable diffusion casings, a pH-independent release behavior may be reached by covering cores, such as non-disintegrating tablets or pellets, with a casing of 20 to 90% of water-insoluble film former (e.g. ethyl cellulose) and 10 to 80% of a water-soluble, elutable component, such as for example polyethylene glycol, methyl cellulose or polyvinyl pyrrolidone. Especially favorable results (in particular, an esp. slight standard deviation of the permeability of the casing) are reached, if certain conditions of production are kept constant. Such standard conditions are besides influencing values such as expansion and disintegration behavior of the cores, composition of the mixture of solvents used for applying the casing, thickness of the diffusion casing, etc.—in particular, the keeping up of a very high spray rate, standardization of the water content of the solvent when it hits the tablet cores, as well as heating of the spray air. A low deviation from the release rate is thereby guaranteed.

Furthermore, it is advantageous, in case tablet-cores are employed, to prepare them as so-called non-disintegrating tablets.

A further advantageous measure, even a necessary one for many active substances (in particular difficultly soluble, basic ones), is the adjusting of an acid medium in the interior of the casing, that is, in the core. It is especially advantageous to influence the pH-medium within the casing with acid materials having a controlled dissolution rate.

It could be proved, that by a gradation of the dissolution retardation of acid tablet excipients-a delay directed to the penetration capacity and solubility of the active substance concerned—the course of release of basic substances in the intestinal fluid may be made almost pH-independent over nearly the total period of function of the depot form.

As acid substances may be considered, in particular, organic acids, such as citric acid, tartaric acid, etc.

Retardation of dissolution of the acid excipients may be reached, for example, by micro-encapsulation or by more or less intensive partial covering of finely crystalline substances with insoluble film-forming substances of the type of ethyl cellulose or insoluble Eudragit ®-types (polymeric lacquer substances on acrylate or methacrylate basis), but also by using polyactide (anhydride of lactic acid) or employing malic acid (difficultly soluble in aqueous medium). A further possibility is to convert the active substance itself (often only weakly basic) by reacting it with a strong acid to form a salt which reacts acid in an aqueous medium.

For some pharmaceuticals, such as the active substance dipyridamole, those substances of acid reaction which form with the active substance dipyridamole in an up to triple molar quantity very good water-soluble masses (>1 gm/ml), such as tartaric acid or citric acid, are primarily suitable. When adding somewhat more water—for example, 5 parts by weight/1.5–6 parts tartaric acid/2 ml water—a syrupy water-clear mass that hardens later by itself is formed, which gives problems during granulation.

In the production of dipyridamole granulates with the aid of suitable acids the quantity of granulating liquid must be particularly observed; that means that not too much water must be added if the granulation process is to run smoothly.

In order to obtain a linear release behavior, it is further important that a certain maximum core volume $V_C$ is not exceeded. This volume depends on the relative solubility of the active substances $S_{rel}$ (=soluble quantity X dose) as well as on the percentage of the dose $X_L$, which is released linearly, described by the following equation:

$$X_L = 100 \cdot (1 - S_{rel} \cdot V_C)$$

As an evaluation criterion whether there is a release of zero order, the proportion of the periods of time required for a 90% and 50% release of active substance ($t_{90\%}/t_{50\%}$) may be used. For a reaction of zero order this value is 1.8; for a reaction of the first order it is 3.3, and for a reaction of the second order it is 9.0.

A further improvement of the release behavior of the retard forms with an acid-containing core may be obtained by adding to the diffusion casing besides an insoluble component and a component soluble in each pH-range, also up to 80% of a component which is only elutable above pH 6. Here may be considered substances such as, for example, cellulose acetate phthalate (CAP), hydroxypropylmethyl cellulose phthalate (HPCP) or partially esterified polymethacrylic acid to which a softening agent is optionally added.

The depot forms produced in accordance with the above indications show a pH-independence of the active substance release up to very high percentages. They may be compounded individually or combined into larger dosage units. This may be done, for example by inserting a core without any retardation effect together with several other cores having semi-permeable diffusion casings of increasing permeability (caused by increasing thickness or varying composition of the casing) into one gelatin capsule. In this manner a release rate of the first core which increases with time can be equalized with a release rate of the subsequent cores which decrease with time.

This retard form is especially suited for cases where, with a very great relative solubility of active substance $S_{rel}$, the core volume $V_C$ cannot be decreased correspondingly for technological reasons, or if the release of acid in the core cannot be adjusted exactly to the release of active substance. For active substances with decreasing absorbability during passage through the gastrointestinal tract or if thrustwise absorption is desired, this special type delivers good results.

The following examples describe the production and composition of several retard forms according to the present invention.

EXAMPLE 1

Etilefrin Preparations

The sympathicomimetic 1-(3-hydroxyphenyl)-2-ethyl-aminoethanol(1), known under the generic name etilefrin, which acts in a dosage range from 5–100 mgm, is an extremely water-soluble substance (about 660 mgm/ml at 25° C. in the pH-range from 1–8). It is therapeutically desirable for etilefrin to reach a high plasma level after only about 2 hours and to let it decrease over a total period of 8 hours.

EXAMPLE 1-a

Etilefrin Retard Form

The table cores are produced in the usual way by admixing the active substance with conventional excipients such as lactose, polyvinyl pyrrolidone and a food color, granulating the moist mixture and compressing the homogeneous mixture into arched cores of about 5 mm diameter ("non-disintegrating tablets" without addition of disintegrant). For the initial tablet there is produced a core with 8 mgm of active substance, and it is covered with a coating which quickly dissolves made of hydroxypropyl methyl cellulose (90%) and polyethylene glycol (10%). Then it is dried.

Furthermore, there are produced per intial tablet four retard tablets. They contain each 4.25 mgm of active substance and are covered with a spray solution by means of a common spray gun, the solution being composed as follows:

| | |
|---|---|
| Ethyl cellulose N 14 | 6 parts |
| Polyethylene glycol 6000 | 4 parts |
| Ethanol (denatured 0.3% H₂O) | 45 parts |
| Methylene chloride | 45 parts |

For retardation stage 1, a quantity of lacquer of 4 mgm is applied, for retardation stage 2 double the quantity (8 mgm). Afterwards the coated tablets are dried.

As the last step, encapsulation of the initial tablet together with each two retard tablets of the two produced retardation stages in hard gelatin capsules by means of a filling device follows.

One single administration of this unit suffices in order to obtain a therapeutic effect reached after administering three times the quantity of etilefrin tablet at an interval of 1.5 hours, so that dosing is considerably simplified for the physician. Besides, fewer side-effects occur (for example, tachycardia) and the intensity of action is greater on the whole.

Retard form of a combination etilefrin/DHEMS

The novel form is also especially suitable for the production of combination preparations of the etilefrin, for example with dihydroergotamine. With such a preparation treatment of the so-called orthostase-syndrome may be started. As the dosage of the dihydroergotamine may be much lower with such a preparation than that of the etilefrin (0.5–10 mgm compared to 5–100 mgm), and as this active substance in the form conventionally used as methane sulfonate is much more difficultly soluble than etilefrin, it suffices to add to the above described etilefrin retard unit one further initial tablet with the active substance dihydroergotamine methane sulfonate (DHEMS).

The cores are produced in the same manner as indicated for the single preparation. In addition to the 5 etilefrin cores with 8 mgm or 4×4.25 mgm of active substance, a further core is produced with 2.5 mgm of dihydroergotamine methane sulfonate (DHEMS).

The coatings are also produced in the manner indicated for the single preparation. Here, the core containing the DHEMS is coated in the same way as the etilefrin initial tablet. Coating of the retard tablets as well as filling of the finished tablets into capsules is done in the same manner as for the single preparation, where capsules are used which can take up a total of 6 tablets of 5 mm diameter.

EXAMPLE 1-b

Etilefrin tablet cores (so-called "non-disintegrating tablets" without disintegrant) produced in the usual way by moist granulation and pressing, of about 5 mm diameter and 50 mgm weight, were coated with a spray solution by means of a normal spray gun, the solution being composed as follows (the parts are parts by weight):

| | |
|---|---|
| Ethyl cellulose N 14 | 7 parts |

-continued

| | |
|---|---|
| (= content of ethoxyl 47.5–49%, viscosity 14 cps) polyethylene glycol (Polywax ® 6000) (average mol. wt. = 6000) | 3 parts |
| Ethanol denatured (0.6% water) | 45 parts |
| methylene chloride | 45 parts |

In doing so, the following conditions were always kept constant:

```
size of boiler
quantity of coating
batch size
spray device
spray distance
duration of drying
spray rate
water content of solvent
temperature of spray air.
```

EXAMPLE 1-c

Etilefrin Preparation

1. Core

| | |
|---|---|
| (a) Etilefrin | 20.0 mgm |
| (b) Tartaric acid (size of particles 0.3–0.6 mm in normal logarithmic distribution) | 25.0 mgm |
| (c) Lactose | 59.7 mgm |
| (d) Magnesium stearate | 0.3 mgm |
| | 105.0 mgm |

Substances a and b are granulated moistly, admixed after drying with substances c and d and pressed into tablets.

2. Coating

In a coating pan under air drying the tablets are sprayed with a 5% solution of ethyl cellulose (4 parts), polyethylene glycol, mol. weight 5000–7000 (1 part), triacetine (0.4 parts) and cellulose acetate phthalate (4.6 parts) in an aqueous mixture of ethanol and methylene chloride, until a polymer quantity of 12 mgm/tablet core is applied.

EXAMPLE 2

Clonidine Retard Form

The antihypertensive 2-(2,6-dichlorphenyl-amino)-2-imidazoline, known under the generic name clonidine, is as a salt (for example, HCl salt) an intensely water soluble substance. It is therapeutically desirable for clondine to cover a period of 24 hours in such a way that the highest plasma level is reached after 4 hours and is kept up to the 10th hour at least, whereupon it should decrease slowly up to the 24th hours.

The tablet cores are produced in the usual way by admixing the active substance with conventional excipients such as lactose, polyvinyl pyrrolidone and a food color, granulating the moist mixture, and pressing of the homogeneous mixture into arched cores of about 5 mm diameter "non-disintegrating tablets" without addition of disintegrant). For the initial tablet there is produced a core with 5 mcg of active substance, and it is covered with a coating which dissolves quickly in an aqueous medium made of hydroxypropyl methyl cellulose (90%) and polyethylene glycol (10%). Then it is dried.

Furthermore, there are produced per initial tablet four retard tablets. They each contain 50 mcg of active substance and are covered with a spray solution by means of a common spray gun, the solution being composed as follows:

| | |
|---|---|
| Ethyl cellulose N 14 | 5 parts |
| Polyethylene glycol 6000 | 5 parts |
| Ethanol (denatured, 0.3% H₂O) | 45 parts |
| Methylene chloride | 45 parts |

For retardation stage 1, there is applied a quantity of lacquer of 5 mgm, for retardation stage 2 double the quantity (10 mgm). Retardation stage 2 is coated in addition with a colored suspension which gives a soluble coating. Then, the coated tablets are dried.

As the last step, encapsulation of the initial tablet together with each two retard tablets of the two produced retardation steps in hard gelatin capsules by means of a filling device follows.

The novel retard form achieves—compared to the Clonidine forms on the market—a reduction of the frequency of administration due to the considerable prolongation of the duration of action as well as an avoidance of frequency and intensity of the side-effects (inter alia dryness of mouth). This goes for doses in the indicated range of 250 mcg as well as elevated doses of 450 or 500 mcg. However, the novel form may be applied in the total range of doses from 0.1–1.5 mgm with favorable results.

The novel form is also especially suitable for the production of combination preparations of the clonidine with other anti-hypertensive active substances, for example with chlorothalidone or hydrochlorothiazide. With such a preparation the dose of the second active substance is essentially higher than that of the clonidine (10–50 mgm compared to 0.05–1.5 mgm). Therefore, it suffices to add to the clonidine retard unit described above one further initial tablet with the second active substance.

Retard Form of a Combination Clonidine/Chlorothalidone

The cores are produced in the same manner as indicated for the single preparation. In addition to the 5 clonidine cores with 5 mcg of active substance a further core is produced with 15 mgm of chlorothalidone.

The coatings are also produced in the manner indicated for the single preparation. Here, the core containing the chlorothalidone is coated in the same way as the clonidine initial tablet. Coating of the retard tablets as well as filling of the finished tablets into capsules is made analogous to the single preparation, where capsules are used which can take up a total of 6 tablets of 5 mm diameter.

EXAMPLE 3

Fenoterol Retard Form

The broncholytic and tocolytic active 1-(3,5-dihydroxy-phenyl)-1-hydroxy-2-[(4-hydroxyphenyl)-isopropylamino]-ethane, known under the generic name fenoterol, is as a salt, a substance easily water-soluble(c.g. hydrobromide). The conventional dosage range lies between 2.5 and 30 mgm.

The cores are produced in the usual way by admixing the active substance with conventional excipients such as lactose, polyvinyl pyrrolidone and a food color, granulating the moist mixture and pressing the homogenous mixture into arched cores of about 5 mm diameter ("non-disintegrating tablets" without addition of disintegrant). For the initial tablet there is produced a core with 2.2 mgm of active substance and it is covered with a coating which dissolves quickly in an aqueous medium made of hydroxypropyl methyl cellulose (90%) and polyethylene glycol (10%). Then it is dried.

Furthermore, there are produced retard tablets. They each contain 1.6 mgm of active substances and are covered with a spray solution by means of a normal spray gun, the solution being composed as follows:

| | |
|---|---|
| Ethyl cellulose N 14 | 5 parts |
| Polyethylene glycol 6000 | 5 parts |
| Ethanol (denatured, 0.3% water) | 45 parts |
| Methylene chloride | 45 parts |

For retardation stage 1, there is applied a quantity of lacquer of 9 mgm, for retardation step 2 a quantity of 12 mgm. Afterwards, the coated tablets are dried.

As the last step, encapsulation of the initial tablet, for example, together with 3 retard tablets of the second retardation stage into hard gelatin capsules by means of a filling device, follows.

The retard form described above achieves the adjustment of a constant plasma level between 1.5 to 5.5 hours after a quick increase of the plasma level. Thus, the range of action of two conventional fenoterol tablets of 2.5 mgm each is covered, that is, it is avoided to administer tablets several times, and at the same time extreme deviations of the plasma level are avoided. This is especially important for tocolytic administration of fenoterol. According to the latest research, a continuous covering of the uterus-receptors must be endeavored.

In particular, the novel form is suitable as well for the production of combination preparations of fenoterol, for example with the active substance ipratropium bromide (=8r=8=isopropyl-3α-[±tropolyloxy]-1αH,-5αH-tropanium bromide) which is useful for the treatment of obstructive respiratory diseases. For the second active substance the dose is higher for such a preparation than that of the fenoterol (7.5–50 mgm, compared to 3.5=30 mgm). It suffices to add to the above described fenoterol retard unit one further initial tablet with the active substance ipratropium bromide as described in the following:

Retard Form of a Combination Fenoterol/Ipratropium Bromide

The fenoterol cores are produced in the same manner as indicated for the single preparation, but with half the quantity of active substance. In addition to the 4 fenoterol cores with 1.1 mgm or 3×0.8 mgm of active substance, there is produced a further core with 7.5 mgm of ipratropium bromide by means of granulating the active substance together with the excipients lactose, corn starch, and magnesium stearate and pressing. The core is coated with an aqueous film, for example made of 30% polyethylene glycol, 20% talcum, 5% TiO₂, a sufficient coloring quantity of a food color lacquer, and 40% hydroxypropyl methyl cellulose.

The coatings for the fenoterol cores are produced in the manner indicated for the single preparation. Coating of the retard tablet as well as filling of the finished tablet into capsules is done as described for the single preparation, whereby capsules are used with can accommodate 5 tablets with 5 mm diameter.

EXAMPLE 4

Mexiletine Retard Form

The antiarrhythmic 1-(2,6-dimethyl-phenoxy)-2-amino-propane, known under the generic name mexiletine, is as a salt (for example an HCl salt) easily soluble in water. With mexiletine it is therapeutically desirable to obtain a slow increase of the plasma level with prolonged plateau formation. The conventional dose lies between 0.1 and 1.5 gm.

The tablet cores are produced in the usual way by admixing the active substance with conventional excipients such as lactose, polyvinyl pyrrolidone and magnesium stearate, granulating the moist mixture, and pressing the homogeneous mixture into arched cores of about 6.2 mm diameter ("non-disintegrating tablets" without addition of disintegrant).

There are produced 6 retard tablets of the same (moderate) retardation stage. They each contain 72 mgm of active substance and are coated with a spray solution by means of a normal spray gun, the solution being composed as follows:

| | |
|---|---|
| Ethyl cellulose N 14 | 6 parts |
| Polyethylene glycol 6000 | 4 parts |
| Ethanol (denatured, 0.3% water) | 45 parts |
| Methylene chloride | 45 parts |

For the retardation stage 1, a quantity of lacquer of about 6 mgm is applied. Then, the coated tablets are dried.

As the last step, encapsulation of the 6 retard tablets thus produced into hard gelatin capsules by means of a filling device follows.

The above example describes a mexiletine form, leading to an optimal release curve in the above sense (slow increase with prolonged plateau formation), but where only minor central side effects occur (vertigo, nausea). Due to the longer duration of action, there occurs, moreover, a distinct simplification of the dosing scheme.

EXAMPLE 5

Bunitrolol Retard Form

The β-adrenolytic 1-(-2-cyano-phenoxy)-3-tert butylamino-propanol(2), known under the generic name bunitrolol, is an easily water-soluble substance in salt form (for example as hydrochloride). The conventional dose range is from 10–150 mgm.

The tablet cores are produced in the usual way by admixing the active substance with conventional excipients such as lactose, polyvinyl pyrrolidone and food color, granulating the moist mixture, and pressing the homogeneous mixture into arched cores of about 5 mm diameter "non-disintegrating tablets" without addition of disintegrant). For the initial tablet there is produced a core with 10 mgm of active substance, and it is covered with a coating which dissolves quickly in an aqueous medium, made of hydroxypropyl methyl cellulose (90%) and polyethylene glycol (10%). Then it is dried.

Furthermore, there are produced per initial tablet two retard tablets. They each contain 10 mgm of active substance and are covered with a spray solution by means of a common spray gun, the solution being composed as follows:

| Ethyl cellulose N 14 | 5 parts |
|---|---|
| Polyethylene glycol 6000 | 5 parts |
| Ethanol (denatured, 0.6% H$_2$O) | 45 parts |
| Methylene chloride | 45 parts |

For the retardation stage 1 a quantity of lacquer of 6 mgm is applied. Then the coated tablets are dried.

At the last step, encapsulation of the initial tablet together with each two retard tablets of the prepared retardation stage into hard gelatin capsules by means of a filling device follows.

In this manner, a quick increase of the plasma level with prolonged plateau formation is obtained. The dosage unit thus obtained simplifies the dosage scheme of the β-adrenolytic considerably and reduces the danger of involuntary overdosing, which should not be underrated with β-adrenolytics. Furthermore it leads to a degradation of the side effects (based upon plasma tops), such as too strong a decrease of blood pressure or strong bradycardia.

The novel form is also suitable for the production of combination preparations of bunitrolol, for example with antihypertonics such as hydrochlorothiazide and/or triamterene, or blood-vessel dilating agents such as isosorbide dinitrate.

The dose of the mentioned antihypertonic in such a preparation may be 5–50 mgm or 10–50 mgm (bunitrolol: 10–150 mgm, preferably 30 mgm). In the combination preparation with isosorbide dinitrate a dose of 10–150 mgm, preferably 30 mgm of isosorbide dinitrate may be combined. It suffices to add to the above bunitrolol retard unit one or several initial tablets with the additional active substances, as shown in the following:

Retard Form of a Combination Bunitrolol/Hydrochlorothiazide/Triamterene

The bunitrolol cores are produced in the same manner as indicated above. In addition to the 3 bunitrolol cores with each 10 mgm of active substance, there produced a further core with 12.5 mgm of hydrochlorothiazide and one core with 25 mgm of triamterene, by admixing the active substance together with lactose, corn starch, and magnesium stearate and food-color, and pressing the mixture.

The coatings are also produced in the manner indicated for the single preparation. Here, the cores containing the additional active substances are coated in the same way as the bunitrolol initial tablets. Coating the bunitrolol retard tablets as well as filling the finished tablets into capsules is effected as described for the single preparation, where capsules are used which can accommodate a total of 5 tablets with 5 mm diameter.

EXAMPLE 6

Codeine Phosphate Retard Form

The analgesic codeine is a substance which is moderately water-soluble in salt form (for example as phosphate), and is administered generally in a dosage range between 15–150 mgm, preferably 25–75 mgm.

An optimal release curve for the codeine phosphate (reaching the highest plasma level after about 2 hours, then plateau formation with subsequent slow decrease over 8–10 hours) is achieved with the depot form described in the following example:

The tablet cores are produced in the usual way by admixing the active substance with conventional excipients such as lactose, polyvinyl pyrrolindone and a food color, granulating the moist mixture and pressing the homogenous mixture into arched cores of about 5 mm diameter "non-disintegrating tablets" without addition of disintegrant). For the initial tablet there is produced a core with 20 mgm of active substance, and it is covered with a coating which dissolves quickly in an aqueous medium, made of hydroxypropyl methyl cellulose (90%) and polyethylene gylcol (10%). Then it is dried.

Furthermore, there are produced per initial tablet four retard tablets. They each contain 10 mgm of active substance and are coated with a spray solution by means of a common spray gun, the solution being composed as follows:

| Ethyl cellulose N 14 | 5 parts |
|---|---|
| Polyethylene glycol 6000 | 5 parts |
| Ethanol (denatured, 0.3% H$_2$O) | 45 parts |
| Methylene chloride | 45 parts |

For the retardation step there is applied a quantity of lacquer of 6 mgm. Then, it is coated with a colored suspension, giving a soluble coating, and dried.

As the last step, encapsulation of the initial tablet together with three retard tablets of the produced retardation stage into hard gelatin capsules by means of a filling device follows.

One single administration of this retard unit corresponds approximately to a dose of 25 mgm of unretarded codeine phosphate administered twice over a time period of three hours; however, the second course of the plasma level curve is considerably more uniform. The novel retard form simplifies very much the dose scheme for the physician and improves compatibility.

The novel retard form is also particularly suitable for production of combination preparations of the codeine phosphate, for example with the analgesic active substance doxylamino succinate. In this preparation the doxylamino succinate dose may be lower than that of the codeine phosphate (5–50 mgm, compared to 10–150 mgm). It suffices to add to the above codeine phosphate retard unit one further initial tablet with the active substance of doxylamino succinate, as described in the following.

Retard Form of a Combination Codeine Phosphate/Doxylamino Succinate

The cores are produced in the same manner as indicated for the single preparation. In addition to the 4 codeine phosphate cores with 20 mgm or 3×10 mgm of active substance, there is produced a further core with 10 mgm doxylamino succinate by granulating the active substance together with lactose corn starch, colloidal silicic acid, soluble starch and magnesium stearate, and pressing the mixture.

The coatings are also produced in the manner indicated for the single preparation. Here, the core containing the doxylamino succinate is coated in the same manner as the codeine phosphate initial tablet. Coating of the retard tablet as well as filling the finished tablets into capsules is effected analogous to Example 1, where capsules are used that accommodate 5 tablets with 5 mm diameter.

EXAMPLE 7

Retard form of
2-amino-6ethyl-4,5,7,8-tetrahydro-6H-oxazolo-[5,4d]-azepine dihydrochloride.

The antihypertensive and anti-anginal substance described in the following example is an easily water soluble substance in salt form (for example, as dihydrochloride).

The tablet cores are produced in the usual way by admixing the active substance with conventional excipients such as lactose, polyvinyl pyrrolidone and a food color, granulating the moist mixture, and pressing the homogeneous mixture into arched cores of about 5 mm diameter ("non-disintegrating tablets" without addition of disintegrant). For the initial tablet there is produced a core with 5 mgm of active substance, and it is covered with a coating which dissolves quickly in an aqueous medium, made of hydroxypropyl methyl cellulose (90%) and polyethylene glycol (10%). Then it is dried.

Furthermore, there are produced per initial tablet three retard tablets. They each contain 5 mgm of active substance and are coated with a spray solution by means of a common spray gun, the solution being composed as follows:

| Ethyl cellulose N 14 | 8 parts |
| Polyethylene glycol 6000 | 2 parts |
| Ethanol (denatured, 0.3% H₂O) | 45 parts |
| Methylene chloride | 45 parts |

For the retardation stage, a quantity of lacquer of 3 mgm is applied. Subsequently, the coated tablets are dried.

If possible, all procedures should be performed under exclusion of water, because the active substance is unstable in the presence of water.

As the last step, encapsulation of the initial tablet together with each 2 retard tablets of the two produced retardation stages into hard gelatin capsules by a filling device follows.

With the novel retard form it is possible to obtain a uniform course of the plasma level and to suppress undesired side-effects (for example, a temporarily too strong decrease of the blood pressure). Furthermore, the dosage scheme for the physician is simplified.

EXAMPLE 8

Dihydroergotamino methanesulfonate (DHEMS) Retard form

| 1. Core | | |
|---|---|---|
| (a) Dihydroergotamino methanesulfonate | 0.5 | mgm |
| (b) Lactose | 26.9 | mgm |
| (c) Citric acid (particle size 0.3–0.6 mm in normal logarithmic distribution) | 20.0 | mgm |
| (d) Ethyl cellulose | 2.4 | mgm |
| (e) Magnesium stearate | 0.2 | mgm |
| | 50.0 | mgm |

Substance c is coated with substance d in a fluidized bed, and substance a is granulated moist with substance b. After admixing the components with substance e, there are pressed corresponding tablets arched on both sides of 5 mm diameter.

2. Coating

In a coating pan with air-drying the tablets are sprayed with a 5% solution of ethyl cellulose (3 parts) and polyethylene glycol, mol. weight: 5000–7000 (7 parts) in an aqueous mixture of ethanol/methylene chloride until a polymer quantity of 6 mgm per tablet core is applied.

EXAMPLE 9

Papaverine Retard form

| 1. Core | | |
|---|---|---|
| (a) Papaverine | 10.0 | mgm |
| (b) Lactose | 18.6 | mgm |
| (c) Citric acid (particle size 0.3–0.6 mm in normal logarithmic distribution) | 20.0 | mgm |
| (d) Ethyl cellulose | 1.2 | mgm |
| (e) Magnesium stearate | 0.2 | mgm |
| | 50.0 | mgm |

The core is produced as described in Example 8.

2. Coating

The coating is also produced as described in Example 8, but 4 parts of ethyl cellulose and 6 parts of polyethylene gylcol (mol. weight 5000–7000) are used. The coating is applied up to a polymeric quantity of 9 mgm per tablet core.

EXAMPLE 10

Quinidine Sulfate Retard Form

The antiarrhythmic quinidine (mostly used as sulfate) is a substance relatively difficultly soluble in water. The dose range lies between 150–1500 mgm. Here it is advantageous to produce all unretarded initial tablets in easily disintegratable condition (for example by addition of corn starch and/or microcrystalline cellulose). Furthermore, it is important to add acid substances (e.g. organic food acids) to the retard tablets in order to improve solubility of the active substance in the interior of the coating.

The easily disintegrating initial tablets are produced by admixing the active substances with the excipients corn starch, polyvinyl pyrrolidone, colloidal silicic acid, mocrocrystalline cellulose as well as magnesium stearate, granulating the moist mixture, and pressing the homogeneous mixture into arched cores of about 6.2 mm diameter. The cores of the retard tablets are prepared without corn starch, but citric acid is added. For the initial tablets (two each per unit) cores with 50 mgm of active substance are produced and they are coated with a coating which disintegrates quickly in an aqueous medium made of hydroxypropylmethyl cellulose (90%) and the polyethylene gylcol (10%). Then it is dried.

Furthermore, 4 retard tablets are prepared per unit. They also each contain 50 mgm of active substance and are coated with a spray solution applied by means of a normal spray gun, the solution being composed as follows:

| Ethyl cellulose N 14 | 6 parts |
| Polyethylene glycol 6000 | 4 parts |
| Ethanol (denatured, 0.6% water) | 45 parts |
| Methylene chloride | 45 parts |

For the used retardation stage, a quantity of lacquer of 5 mgm is applied. Then the coated tablets are dried.

As the last step, encapsulation of the two initial tablets together with four retard tablets of the produced retardation stage into hard gelatin capsules by means of a filling device follows.

The novel form simplifies the dosage scheme of the physician considerably. Furthermore, it avoids (by peaks of plasma level) easily occurring, excessively strong effects, which is of special importance for an antiarrhythmic.

The novel form is also suitable for production of combination preparations of quinidine, the additional active substance of which may be incorporated into a further initial tablet.

EXAMPLE 11

Dipyridamole Retard Form

The coronary therapeutic dipyridamole, used as the base, is a substance relatively difficultly soluble in water; it is used in a dose range of 150–400 mgm.

Especially suitable excipients for cores for a retard form with pH-independent release are those substances of acid reaction which form with the active substance dipyridamole in one to triple molar quantity very good water-soluble (>1 gm/ml) masses, such as tartaric acid or citric acid. By addition of some more water-for example, 5 parts by weight/1.5–6 parts by weight tartaric acid/2 ml water—a syrupy water-clear mass is formed which hardens by itself later, which gives problems during granulating.

Therefore, when producing the dipyridamole granulates with the aid of suitable acids, the quantity of the liquid for granulation (water) must be taken account of; too much water should not be added if the granulation procedure is to run smoothly.

The easily disintegrating initial tablets are produced by admixing the active substances with conventional excipients such as lactose, corn starch, etc., granulating the moist mixture, and pressing the homogeneous mixture into arched cores of about 6.2 mm diameter. The cores of the retard tablets are made of lactose, tartaric acid (25 mgm) and magnesium stearate. The initial tablet contains 25 mgm of active substance and is coated with a coating which dissolves quickly in an aqueous medium, made of hydroxypropyl methyl cellulose (90%) and polyethylene glycol (10%).

Furthermore, there are produced per unit five retard tablets (as non-disintegrating tablets). They also each contain 25 mgm of active substance and 25 mgm of tartaric acid and are coated with a spray solution by means of a spray gun, the solution having the following composition:

| Ethyl cellulose N 14 | 4 parts |
| Polyethylene glycol 6000 | 6 parts |
| Ethanol (denatured, 0.3% water) | 45 parts |
| Methylene chloride | 45 parts |

For the used retardation stage a quantity of lacquer of 6 mgm is applied. Then the coated tablets are dried.

As the last step, encapsulation of one initial tablet together with five retard tablets of the prepared retardation stage into hard gelatin capsules by means of a filling device follows.

The novel form simplifies the dosage scheme of the physician essentially. Furthermore, it avoids (by peaks of plasma level) easily occurring excessively strong effects, which is of special importance for a cardiac agent.

The novel form is also suitable for production of combination preparations of the dipyridamole, for example with acetyl salicylic acid, where the additional active substance is incorporated into further retard tablets.

EXAMPLE 12

Dipyridamole Retard Form

The tablets are prepared as described in Example 11 and are then coated by spraying with a 5% solution of the following:

| Ethyl cellulose N 14 | 4 parts |
| Polyethylene glycol 6000 | 2 parts |
| Cellulose acetate phthalate | 3.6 parts |
| Triacetin | 0.4 parts | which are dissolved in a water-containing mixture of ethanol and methylene chloride, until each tablet has a coating comprising 4 mgm of lacquer.

Comments to Examples 1, 8, 9, 11 and 12

The release of active substance from the various formulations described in the above examples in artificial intestinal fluids was examined in the Sartorius dissolution model [Pharm. Ind. 33, 446 (1971), and 38, 232, 289 (1976)]. The following results were obtained:

(a) Etilefrin (see Example 1 b and 1 c)

In the release of etilefrin ($pk_a$-values: 2.6; 8.8; 10) from tablets which are covered with a semipermeable diffusion-coating, the pH-value of the solvent (artificial stomach or intestinal fluid) has no influence on the release of active substance from the tablets with coated and noncoated citric acid. This is due to the pH-independent solubility of etilefrin. In the range of pH 1–pH 8 about 600 mgm/ml (25° C.) dissolve in either case. Variation of the composition of the coating shows that in artificial intestinal fluid of pH 7 coatings of 100% ethyl cellulose are substantially impermeable. Coatings of ethyl cellulose with incorporated polyethylene glycol release the active ingredient linearly up to about 60%. This also applies to coatings containing the acid-insoluble polymer hydroxypropyl methyl cellulose phthalate (HPCP), if the tablet cores do not contain added acid.

On the other hand, the rate of active substance release increases with time up to about 60% in the case of acid-containing tablets with coatings consisting partially of the acid-insoluble polymer CAP.

(b) DHEMS (see Example 8)

Dihydroergotamine methane sulfonate (DHEMS, $pk_a = 6.7$), shows a completely different release behavior than etilefrin. From coated tablets without added acid excipients only a very slow release of active substance is effected in the pH-range of the intestines, pH 6.0–pH 7.5. The pH-dependence and the low degree of release is based upon the solubility of DHEMS. It amounts to about $2 \times 10^{-1}$ mgm/ml at pH 6.0 and $2 \times 10^{-2}$ mgm/ml at pH 7.3. The low release rate is significantly increased by addition of acid tablet excipients, such as for example citric acid, but the pH-dependence is not completely eliminated, because in this case the acid excipient diffuses out of the coated preparation more rapidly than the active substance. Only by partial coating of the acid tablet excipient, the consequence of which is a retarded dissolution in the interior of the coated form, can the pH-dependence of the DHEMS-release be eliminated. The optimal degree of coating of the acid excipient depends, inter alia, upon the diffusion properties of the corresponding active substance; for DHEMS it amounts to about 12%. Too strong a retardation of the dissolution of the acid again negatively influences the release of active substance.

(c) Dipyridamole (see Examples 11 and 12)

The strong pH-dependent solubility of the active substance (pH 1:>1000 mgm/l, pH 6:7 mgm/l, pH 7:1 mgm/l) has as a consequence an extremely slow release in the neutral pH-range, if the tablets do not contain any added acid excipients or if the active substance has not been converted into an acid salt (for example, dipyridamole-citrate).

Acid-containing tablets with coatings of ethyl cellulose and a water-soluble polymer release the active substance as a function of time which corresponds to a reaction of first order. If the tablet coatings contain some acid-insoluble polymers, the change of the release rate tends to be inverse: The release rate increases with the time.

The release rate may also be varied by the thickness of the coatings; it is inversely proportional to the latter.

(d) Papaverine (see Example 9)

Similar to DHEMS, papaverine is a weakly basic substance with a $pk_a$-value of 6.4. The solubility is strongly pH-dependent (about 3.8 mgm/ml at pH 3.0, about $5.10^{-2}$ mgm/ml at pH 6.0, and about $2.10^{-2}$ mgm/ml at pH 7.3). Due to the low solubility in the artificial intestinal fluid, the release rate from tablets with diffusion coatings is extremely small. Just as in the case of DHEMS, the release rate is very distinctly increased by acid tablet excipients (for example, citric acid), but the pH-dependence of the release is only eliminated in the beginning.

A partial coating of the acid tablet excipient with an insoluble film-former, for example ethyl cellulose, eliminates the pH-dependence. The optimal degree of coating does not only depend upon the diffusion properties of the active substance, but also upon permeability or thickness of the diffusion-coating, and upon the type and distribution of particle size of the acid excipient.

The optimal quantity for coating of papaverine in the form of acid-containing tablets with 6.0 mgm diffusion coating tablet is about 12 mgm of ethyl cellulose/100 mgm citric acid, and for corresponding tablets with 9.0 mgm diffusion coating/tablet it is 6 mgm of ethyl cellulose/100 mgm of citric acid (anhydrous, particle size 0.3–0.6 mm in normal logarithmic distribution).

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition consisting essentially of a gelatin capsule containing a plurality of non-disintegrating cores comprising mexiletine or an acid addition salt thereof, said cores having a coating consisting of from 20 to 90 percent by weight of a water-insoluble film former and from 10 to 80 percent by weight of a water-soluble polymer, the diameter of each of the cores being at least about 5 mm.

2. The dosage unit composition of claim 1, wherein the mexiletine is present in a total amount of from about 0.1 to 1.5 gm.

3. The dosage unit composition of claim 1, wherein the water-insoluble film former is ethyl cellulose.

4. The dosage unit composition of claim 1, wherein the cores are tablets or pellets.

5. The dosage unit composition of claim 1, wherein the cores have a diameter of from about 5 to 6.2 mm.

6. A method for the treatment of cardiovascular disorders in a host in need of such treatment which comprises administering to said host an effective amount of a composition of claim 5.

* * * * *

UNITED STATES PATENT AND TRADEMARK OFFICE
CERTIFICATE OF CORRECTION

PATENT NO. :   4,459,279

DATED      :   July 10, 1984

INVENTOR(S) :  HERBERT STRICKER et al.

It is certified that error appears in the above-identified patent and that said Letters Patent is hereby corrected as shown below:

Title page [30], the number of priority application "2836477" should read -- 2836447 --.

Column 8, line 60, after "diameter" insert -- ( --.

Column 11, line 4, the moiety "6ethyl" should read -- 6-ethyl --.

Column 16, last line of Claim 6, "claim 5" should read -- claim 1 --.

Signed and Sealed this

Twenty-second Day of January 1985

[SEAL]

Attest:

DONALD J. QUIGG

*Attesting Officer*   *Acting Commissioner of Patents and Trademarks*